US00PP27874P2

(12) United States Plant Patent
Jones et al.

(10) Patent No.: US PP27,874 P2
(45) Date of Patent: Apr. 11, 2017

(54) ***PHYSOCARPUS* PLANT NAMED 'JONIGHT'**

(50) Latin Name: *Physocarpus opulifolius*
Varietal Denomination: JONIGHT

(71) Applicants: John Jones, Newton (GB); Maria Jones, Newton (GB)

(72) Inventors: John Jones, Newton (GB); Maria Jones, Newton (GB)

( * ) Notice: Subject to any disclaimer, the term of this patent is extended or adjusted under 35 U.S.C. 154(b) by 216 days.

(21) Appl. No.: 14/120,949

(22) Filed: Jul. 14, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

New Plants and Flowers Almost black *Physocarpus opulifolius* Oct. 7, 2013, retrieved on Apr. 18, 2016, retrieved from the Internet at <http://www.newplantsandflowers.com/almost-black-physocarpus-opulifolius/> 2 pp.*

CPVO Application for Community Plant Variety Right to the Community Plant Variety Office for Midnight from remarks filed on Jul. 25, 2016, 18 pp.*

* cited by examiner

*Primary Examiner* — June Hwu
(74) *Attorney, Agent, or Firm* — Penny J. Aguirre

(57) ABSTRACT

A new cultivar of *Physocarpus*, 'JONIGHT' that is characterized by its compact, upright and bushy plant habit, its foliage that is very dark purplish-brown to black in color, and its well branched stems with short internodes.

2 Drawing Sheets

Genus/species: *Physocarpus opulifolius.*
Varietal denomination: 'JONIGHT'.

BACKGROUND OF THE INVENTION

The present invention relates to a new and distinct cultivar of *Physocarpus opulifolius* and will be referred to hereafter by its cultivar name, 'JONIGHT'. 'JONIGHT' represents a new cultivar of *Physocarpus*, a deciduous shrub grown for landscape use.

The new *Physocarpus* arose from a breeding program conducted by the Inventors at their nursery in Newtown, The United Kingdom. 'JONIGHT' originated as a seedling that arose from seed pooled and planted derived from open pollination of *Physocarpus opulifolius* cultivars 'Dart's Gold' (not patented), 'Monlo' (U.S. Plant Pat. No. 11,211) in fall of 2008, and unnamed proprietary seedlings. The exact parentage is therefore unknown. The new *Physocarpus* was selected as a single unique plant in 2009.

Asexual propagation of the new cultivar was first accomplished by softwood cuttings in Newton, The United Kingdom by one of the Inventors in 2009. Asexual propagation by softwood cuttings has determined that the characteristics of this cultivar are stable and reproduced true to type in successive generations.

SUMMARY OF THE INVENTION

The following traits have been repeatedly observed and represent the characteristics of the new *Physocarpus*. These attributes in combination distinguish 'JONIGHT' as unique and distinct cultivar of *Physocarpus*.

1. 'JONIGHT' exhibits a compact, upright, bushy plant habit.

2. 'JONIGHT' exhibits foliage that is very dark purplish-brown to black in color.
3. 'JONIGHT' exhibits well-branched stems with short internodes.

'JONIGHT' can be compared to its possible parent plants, 'Monlo' and 'Dart's Gold'. 'Monlo' differs from 'JONIGHT' in having foliage that is a lighter black/green in color, in having larger leaves that are more irregular in size and internodes that are longer in length, in being less branched (more canes), in having a more vigorous growth habit, and in having a larger more erect plant habit. 'Dart's Gold' differs from 'JONIGHT' in being larger in size and in having foliage that is yellow to chartreuse in color. 'JONIGHT' can also be compared to the cultivars 'Lady in Red' (U.S. Plant Pat. No. 18,660). 'Lady in Red' differs from 'JONIGHT' in being shorter, in having a more compact, bushy plant habit, in having foliage that is red to brown in color, and in having internodes that are shorter in length.

BRIEF DESCRIPTION OF THE DRAWINGS

The accompanying colored photographs illustrate the overall appearance and distinct characteristics of the new *Physocarpus*. The photographs in FIG. 1, FIG. 2, and FIG. 3 were taken of plants about 6 months in age from a liner grown in 2.5-liter containers in Maldon, Essex, The United Kingdom.

Figure 1:
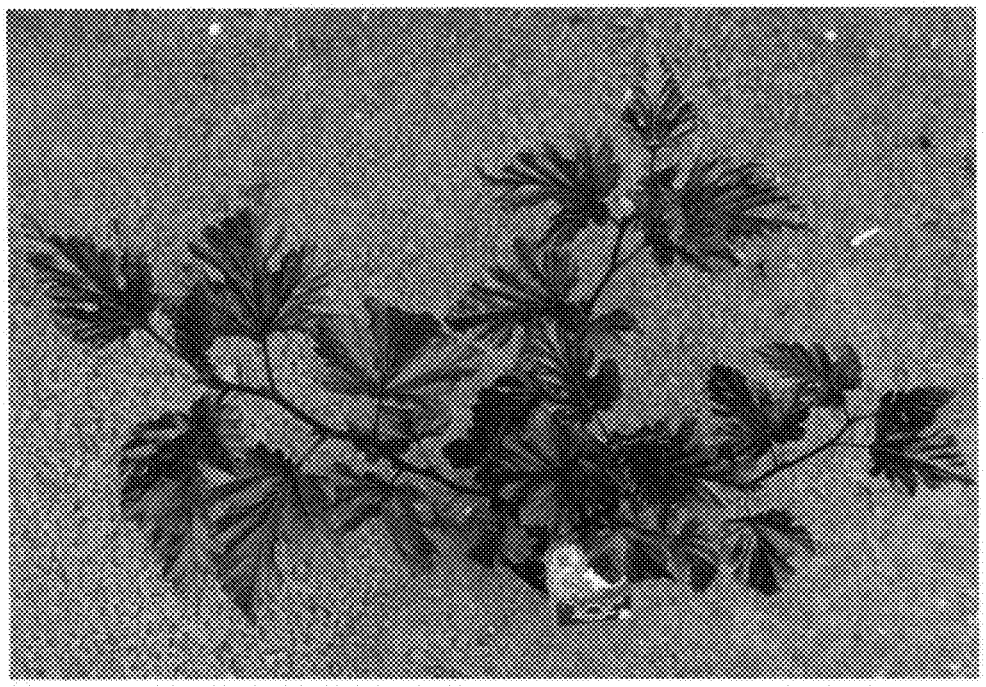
FIG. 1 provides a view of the mature foliage of 'JONIGHT'.
Figure 2:
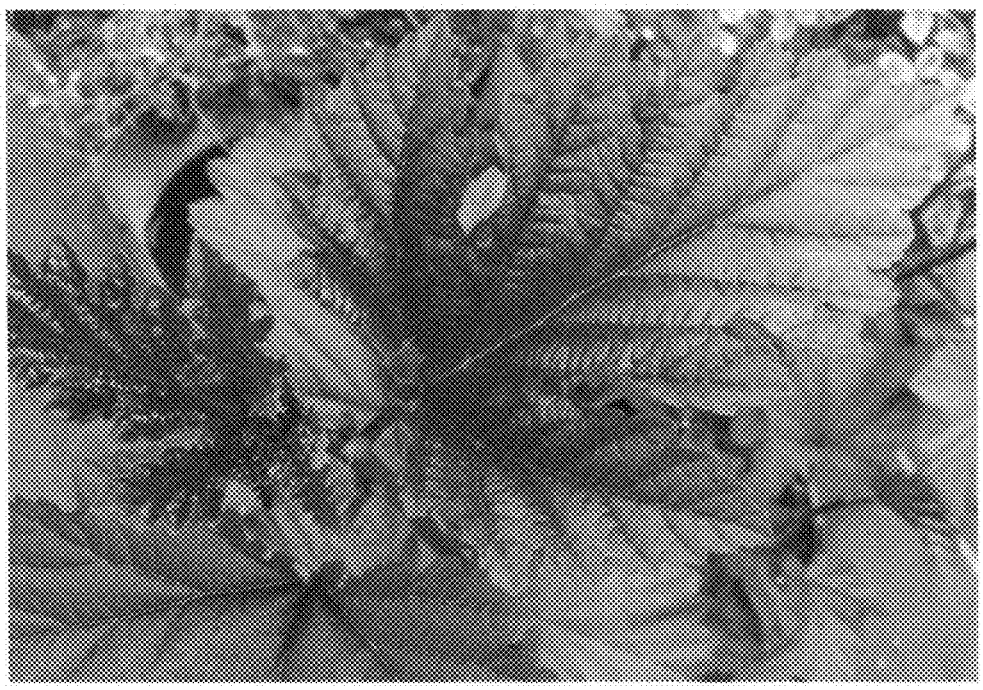

The photograph in FIG. 2 provides a close-up view of the young foliage of 'JONIGHT'.

Figure 3:
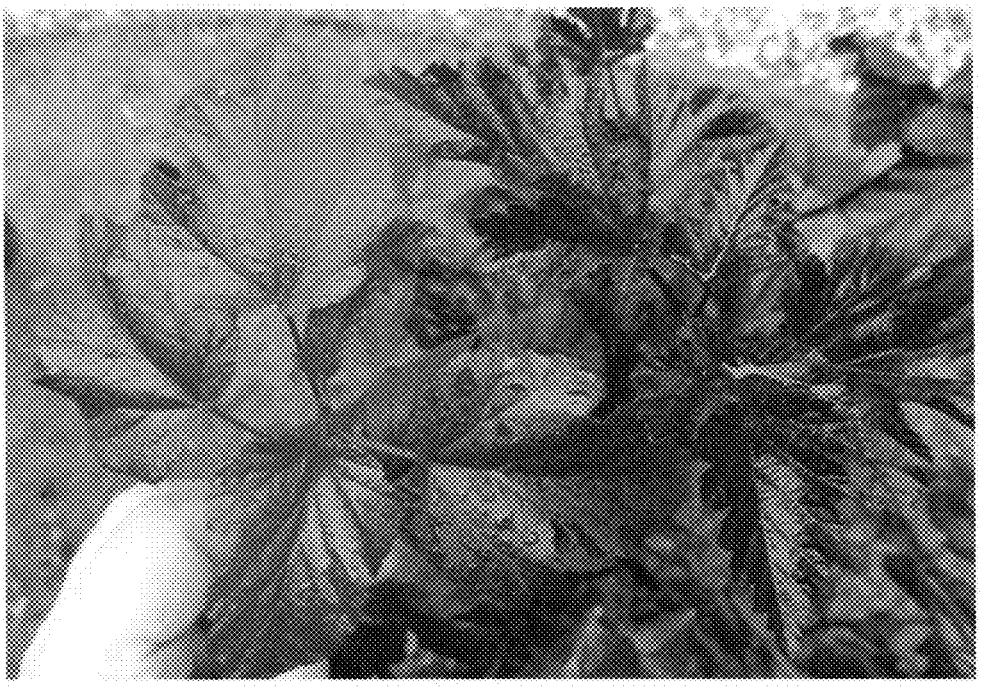

The photograph in FIG. 3 provides a comparison view of the mature foliage of 'Lady in Red' on the left and 'JONIGHT' on the right.

Figure 4:
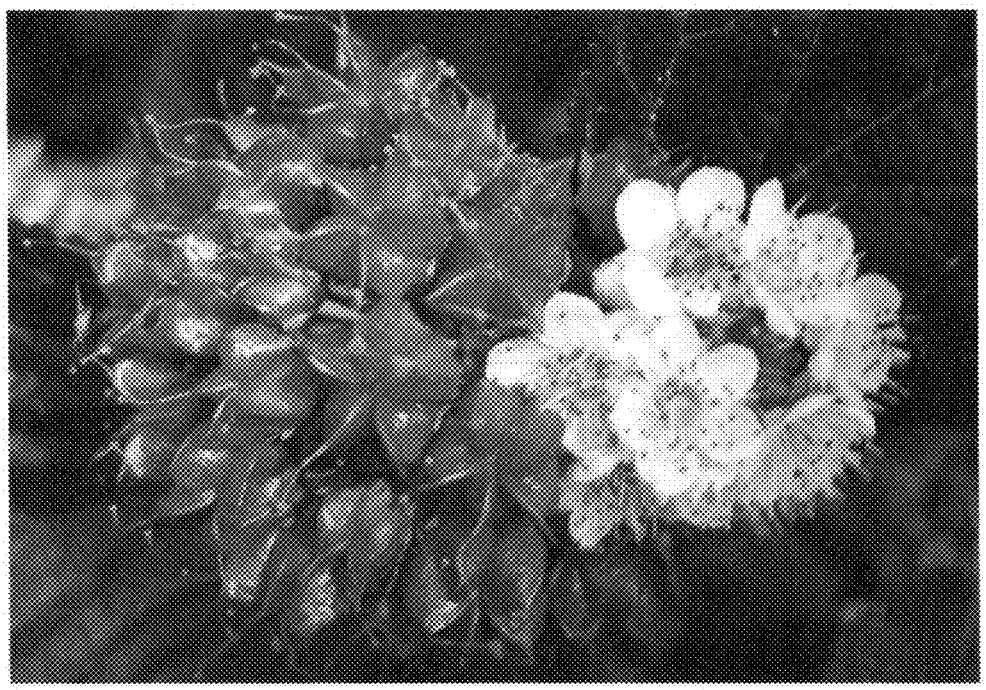

The photograph is FIG. 4 was taken of a plant about 3 years in age as grown in a trial garden in Newtown, The United Kingdom and provides a view of the fruit and flowers of 'JONIGHT'.

The colors in the photograph may differ slightly from the color values cited in the detailed botanical description, which accurately describe the colors of the new *Physocarpus.*

DETAILED BOTANICAL DESCRIPTION OF THE PLANT

The following is a detailed description of one year-old old plants (from a liner) of the new cultivar as grown outdoors in three-liter containers in Liss, The United Kingdom with the mature size and flower and fruit data collected from 3 year-old plants grown outdoors in a trial garden in in Newtown, The United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late spring/early summer on old wood in The United Kingdom.

*Plant habit.*—Upright, well-branched, bushy, deciduous shrub.

*Height and spread.*—An average of 36 cm in height and 18 cm in spread in a 3-liter container, matures to about 1.2 m in height and 60 cm in width in the landscape (if un-pruned).

*Hardiness.*—At least in U.S.D.A. Zone 2.

*Diseases and pests.*—No susceptibility or resistance to diseases or pests has been observed.

*Root description.*—Fibrous.

*Growth rate.*—Moderate.

*Propagation.*—Softwood cuttings.

Branch description:

*Branch color.*—New growth; A blend of 200C and N199B, old wood N199B.

*Branch shape.*—Round to slightly angled.

*Branch aspect.*—Held at an average angle of 70° from vertical.

*Branch size.*—An average of 3 mm in diameter and 30 cm in length.

*Branch surface.*—Glabrous.

*Branching.*—Well-branched; an average of 6 lateral branches in a 3-liter container.

Foliage description:

*Leaf shape.*—Ovate.

*Leaf division.*—Simple.

*Leaf base.*—Weakly cordate.

*Leaf apex.*—Acute.

*Leaf venation.*—Pinnate, color upper surface; N187A, color lower surface; 177A to 177C.

*Leaf margin.*—Three to five lobed with lobes crenate to serrate.

*Leaf attachment.*—Petiolate.

*Leaf arrangement.*—Alternate.

*Leaf surface.*—Glabrous on both surfaces.

*Leaf size.*—An average of 6.5 cm in length and width.

*Internode length.*—An average of 4.25 cm in center of stem.

*Leaf color.*—Young foliage upper and lower surface; a blend of 178A and 178B and suffused with N18713, mature foliage upper surface; a blend of 203A, N186C, and 200A, mature foliage lower surface; N199A and tinged with 138B (closest), fall foliage upper surface; a blend of 187A to 187B and N186C, fall foliage lower surface; 177B to 177C (slightly redder).

*Petioles.*—An average of 2 cm in length and 2 mm in diameter, glabrous surface, a blend of 200B and N186C in color.

*Stipules.*—None.

Flower description (not a distinguishing characteristic):

*Flower type.*—Small rotate flowers arranged in spherical corymb.

*Inflorescence size.*—An average of 3.5 cm in width and depth.

*Flower fragrance.*—Slight.

*Flower lastingness.*—Corymb lasts about Average of 14 to 20 days, not persistent, individual flowers about 3 days.

*Flower bud description.*—Elliptic in shape, average of 3.5 cm in length and 3 mm in diameter, 183D in color.

*Flower quantity.*—About 40 per corymb.

*Flower size.*—About 6 mm in depth and 7.5 mm in diameter.

*Peduncles.*—About 1.4 cm in length and 2 mm in diameter, 144A in color, glabrous surface.

*Pedicels.*—About 1.8 cm in length and 1 mm in diameter, 144A in color, glabrous surface.

*Petal description.*—5, elliptic to obovate in shape, margin is entire, apex is broadly acute, lower and upper surface is glabrous, apex is obtuse, base is attenuate.

*Petal size.*—About 5 mm in length and 4 mm in width.

*Petal color.*—Opening; upper surface N155C and lower surface N155C and blushed with 65D, fully open; upper and lower surface 155D turning slightly greyer as they age.

*Calyx size.*—Average of 7.5 mm in length and diameter.

*Sepal description.*—5, subulate in shape, margin is entire, apex is acute, surface is glabrous.

*Sepal size.*—Average of 1.7 cm in length, 3 mm in width.

*Sepal color.*—Outer and inner surfaces; 144A when developing, turning to 75C after anthesis.

Reproductive organs:

*Gynoecium.*—4, Pistil about 0.5 mm in length, stigma is globular in shape and 145B in color, style is about 1 cm in length and N155C in color, ovary is 145B in color.

*Androecium.*—Numerous, anthers are oblong in shape, about 0.5 mm in length and 197A in color, filaments are about 5 mm in length, pollen is scarce in quantity; too minimum for color reading.

Fruit and seed: Fruit a firm-walled inflated follicle, 5-starred, splitting open at seams, 46C in color, seeds are hard, shiny, ovoid in shape, 155B in color as they start developing and turning darker at maturity.

It is claimed:

1. A new and distinct cultivar of *Physocarpus* plant named 'JONIGHT' as herein illustrated and described.

* * * * *